United States Patent [19]

DeLuca et al.

[11] 4,428,946

[45] Jan. 31, 1984

[54] METHOD OF PREVENTING MILK FEVER IN DAIRY CATTLE

[75] Inventors: Hector F. DeLuca; Heinrich K. Schnoes, both of Madison; Neal A. Jorgensen, Middleton, all of Wis.

[73] Assignee: Wisconsin Alumni Research Foundation, Madison, Wis.

[21] Appl. No.: 401,996

[22] Filed: Jul. 26, 1982

[51] Int. Cl.³ ............................................. A01N 45/00
[52] U.S. Cl. .................................................... 424/236
[58] Field of Search ...................... 424/236; 260/397.2

[56] References Cited

U.S. PATENT DOCUMENTS

| | | | |
|---|---|---|---|
| 4,196,133 | 4/1980 | DeLuca et al. | 260/397.2 |
| 4,199,577 | 4/1980 | Takeshita et al. | 424/236 |
| 4,284,577 | 8/1981 | Yamada et al. | 260/397.2 |
| 4,338,312 | 7/1982 | DeLuca et al. | 424/236 |

*Primary Examiner*—Elbert L. Roberts
*Attorney, Agent, or Firm*—Howard W. Bremer

[57] ABSTRACT

A method for prophylactically treating dairy cattle for parturient paresis by administering to cattle vitamin D derivatives which are characterized by the presence of a hydroxyl group at at least one of the C-1 and C-25 positions and a metabolically stable blocking group at the C-24 position in an amount sufficient to induce said prophylaxsis.

16 Claims, No Drawings

METHOD OF PREVENTING MILK FEVER IN DAIRY CATTLE

This invention was made with Government support under Grant No. NIH AM 14881 awarded by the Department of Health and Human Services. The Government has certain rights in this invention.

DESCRIPTION

1. Technical Field

This invention relates to a method for preventing milk fever (parturient paresis) in dairy cattle.

More particularly this invention relates to a method for preventing milk fever disease in dairy cattle which comprises administering to the cattle vitamin D derivatives which are characterized by the presence of a hydroxyl group of at least one of the C-1 and C-25 positions in the vitamin D molecule and where the C-24 position carries a metabolically stable blocking group.

2. Background Art

Parturient paresis, or milk fever disease, occurs with substantial frequency in high-producing dairy cattle generally beginning with the third and later lactations. The disease involves a hypocalcemia and a hypophosphatemia at the time of parturition or shortly thereafter, resulting in the animal becoming immobilized and flacid. This phenomemon has been clearly related to the low blood calcium resulting from the formation of milk at the time of parturition. However, many animals do not suffer the disease and are able to provide sufficient calcium in their blood from intestinal and bone sources to meet the immediate demands of new milk formation. The reason for the difference among individual animals remains unknown. However, several methods of preventing the disease have been suggested and tried. These are:

(1) calcium infusions, which is the common method of treatment of the disorder;
(2) the administration of large amounts of vitamin D, which will prevent the hypocalcemic response; or
(3) conditioning of animals with either a low calcium diet or an acidic diet.

Unfortunately, large amounts of ordinary vitamin D have not been successful primarly because it can only be given once, and often vitamin D intoxication or calcification of organs (soft tissue) becomes a major concern. Calcium infusions are excellent treatments, but it is not practically possible to prevent the disease by calcium infusion alone, since it is not possible to forecast when milk fever will result from calving. Low calcium conditioning of the animal is not desirable since it is during the non-lactating or dry periods that cows are able to replace the bone calcium which had been depleted by previous lactation. Use of acid diets tends to produce an acidosis that results in other problems. Therefore, none of these treatments has provided a complete solution to the prevention of parturient paresis.

The discovery of active vitamin D metabolites and their analogs has led to the development of more effective methods for treating parturient paresis. Thus, it has been shown that 25-hydroxyvitamin $D_3$, a metabolite of vitamin D, given in relatively large amounts, provides substantial protection against the disease (U.S. Pat. No. 3,646,203). Similarly, much lower doses of $1\alpha$-hydroxyvitamin $D_3$ or 1,25-dihydroxyvitamin $D_3$ have also been shown to be effective in preventing the disease (U.S. Pat. Nos. 3,879,548 and 4,110,446), and the use of a mixture of $1\alpha$-hydroxyvitamin $D_3$ and 25-hydroxyvitamin $D_3$ has recently been proposed as a method for providing very marked protection against milk fever disease (U.S. Pat. No. 4,338,312).

DISCLOSURE OF INVENTION

During the course of investigations of milk fever disease, it was found that the cows that come down with the disease have above normal average blood levels of 24,25-dihydroxyvitamin $D_3$, a metabolite of vitamin D. This observation, suggested a possible causal relationship between circulating 24,25-dihydroxyvitamin $D_3$ and the disease and led to further studies in which this metabolite was administered to cows prior to parturition.

A herd of dairy cattle at third lactation or better was divided randomly into two groups of 28 cows each. The non-treated group (control group) received an intramuscular injection of corn oil without vitamin D compound dissolved in it, whereas the treated group received the same dose of oil containing 24,25-dihydroxyvitamin $D_3$ (4 mg/animal). The results of this experiment are shown in Table 1.

TABLE 1

Effect of 24,25-Dihydroxyvitamin $D_3$ on Incidence of Parturient Paresis

| Group | Normal No. | Parturient Paresis No. | Incidence % |
|---|---|---|---|
| Control | 24 | 4 | 14 |
| Treated | 14 | 14 | 50 |

It is evident from the data presented in Table 1 that the dairy cattle receiving 24,25-dihydroxyvitamin $D_3$ had a dramatically higher incidence of milk fever (about 50%) than the control group (14% milk fever incidence). It is evident, therefore, that the presence of 24-hydroxylated vitamin D increased the incidence of milk fever, and it appears to predispose the animal to the disease. Re-examination of the plasma levels of 24,25-dihydroxyvitamin $D_3$ in animals that ultimately came down with milk fever disease show (see Table 2) that these animals have higher than normal levels of 24,25-dihydroxyvitamin $D_3$ prior to the onset of milk fever.

TABLE 2

Plasma 24,25-Dihydroxyvitamin $D_3$ Levels of Cows Prior to, at and Following Parturition

| Group | Sampling Time[1] Values in ng/ml | | | | |
|---|---|---|---|---|---|
| | $-3$[2] | $-1$ | 0 | $+1$ | 3 |
| Non-Paretic | 3.2 | 3.3 | 3.0 | 2.8 | 3.0 |
| Paretic | 3.7 | 4.0 | 3.7 | 4.5 | 4.0 |

[1]The indicated times represent the time of calving as 0 and other times are days before and after calving.
[2]Days The foregoing results clearly establish a correlation between 24,25-dihydroxyvitamin $D_3$ and milk fever disease, and indicate that the accumulation of this vitamin D metabolite in the animal is undesirable in the sense that it contributes to a higher incidence of the disease and appears to predispose the animal to it.

It is to be noted that all of the treatments heretofore proposed as the most effective means of preventing milk fever disease, i.e. the use of vitamin D derivatives such as 25-hydroxyvitamin $D_3$, $1\alpha$,25-dihydroxyvitamin $D_3$ or $1\alpha$-hydroxyvitamin $D_3$, involve the administration compounds that are non-hydroxylated at C-24. The data presented in Table 1 and Table 2 lead to the conclusion that the absence of 24-hydroxylation is an important characteristic of an effective anti-milk fever agent. However, all of these vitamin D derivatives can serve, either directly or indirectly, as substrates for enzymatic 24-hydroxylation in vivo in the animals and can give rise to the undesired 24,25-dihydroxy side chain structure (e.g. by the reactions: 25-hydroxyvitamin $D_3 \rightarrow$ 24,25-dihydroxyvitamin $D_3$; $1\alpha,25$-dihydroxyvitamin $D_3 \rightarrow 1\alpha,24,25$-trihydroxyvitamin $D_3$; $1\alpha$-hydroxyvitamin $D_3 \rightarrow 1\alpha,25$-dihydroxyvitamin $D_3 \rightarrow 1\alpha,24,25$-trihydroxyvitamin $D_3$). The occurence, in vivo, of 24-hydroxylation according to the reactions shown, is well established and, hence, the vitamin D compounds now used for the treatment of milk fever disease will unavoidably yield the 24,25-dihydroxy metabolites. This is also true for compounds of the vitamin $D_2$ series, which are known to undergo an analogous sequence of hydroxylation reactions. A further complicating feature is that for any given animal the rates of these in vivo 24-hydroxylation are unknown and unpredictable, being dependent on a number of physiological parameters (e.g. Ca and phosphate status, other hormones, etc.), and hence, the effectiveness of these compounds to combat milk fever may be affected in an unpredictable fashion to the extent that they contribute, by in vivo metabolism to the undesired 24,25-dihydroxy metabolite pool.

Based upon the observation and results described hereinbefore it is clear that successful prophylaxsis against milk fever disease can be achieved by administrating to dairy cattle a vitamin D derivative which retains the structural features known to be important to such activity, namely, hydroxylation at at least one of C-1 and C-25 positions, but which cannot be readily hydroxylated in vivo at the C-24 position.

Suitable compounds for this purpose are, therefore, analogs of the vitamin $D_3$ or vitamin $D_2$ series characterized by the structure

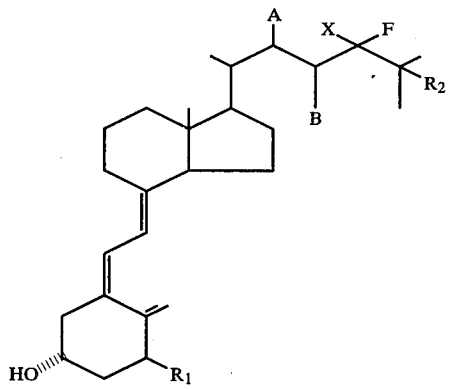

wherein A and B are hydrogen, or taken together form a double bond, wherein X is fluoro, hydrogen or methyl, and where $R_1$ and $R_2$ are selected from hydrogen and hydroxy except that at least one of $R_1$ and $R_2$ must be hydroxy. The hydroxy group at carbon 3 and/or the hydroxy groups at carbons 1 and/or 25 may also be acylated, e.g. be present as the acetyl, propionyl, benzoyl or other conventional acyl derivatives known in the art, such acylated derivatives also being suitable and effective as anti-milk fever agents.

The above compounds are characterized by the presence of a hydroxy group(s) at C-1 and/or 25, which confer high anti-milk fever potency, and a blocking group at carbon 24 in the form of a 24-fluoro, or 24,24-difluoro substituent, the function of which is to prevent the introduction of a 24-hydroxy group during in vivo metabolism.

Specific examples of such compounds are:
24,24-difluoro-25-hydroxyvitamin $D_3$
24,24-difluoro-$1\alpha,25$-dihydroxyvitamin $D_3$
24,24-difluoro-$1\alpha$,-hydroxyvitamin $D_3$
24-fluoro-25-hydroxyvitamin $D_3$
24-fluoro-$1\alpha,25$-dihydroxyvitamin $D_3$
24-fluoro-$1\alpha$-hydroxyvitamin $D_2$
24-fluoro-25-hydroxyvitamin $D_2$ The fluoro substituents in the C-24 position are known to block in vivo hydroxylation and therefore such compounds cannot readily give rise to the 24,25-dihydroxylated forms of vitamin D which in the normal metabolic course in vivo result from the metabolism of any 25-hydroxylated vitamin D compound, however, the above named C-24-fluoro analogs are at least as effective as the corresponding compounds absent the fluoro blocking group at the C-24 position.

Such 24-blocked vitamin D analogs are readily available by synthetic processes known in the art, e.g. as described in U.S. Pat. Nos. 4,305,880, 4,196,133 and 4,229,357. In addition, 1-hydroxylated analogs are also available by combination of chemical and enzymological synthesis as described, for example, in U.S. Pat. Nos. 4,201,881 and 4,226,788. Since the C-24-blocked compounds set forth above are capable of preventing the detrimental accumulation of the 24,25-dihyroxylated vitamin D metabolites in vivo while retaining the desirable vitamin D-like and milk fever combatting characteristics they are eminently suitable for purposes of the present invention and are the preferred compounds for such purpose.

The present invention is practiced by administering any of the 24-blocked vitamin D compounds shown above to cows prior to parturition. Advantageously, the compounds are administered about 3 to 8 days prior to the expected calving date and may be given as a single dose, or, if preferred, as multiple doses over a period of days. Dosage amounts depend on the compound being administered, with 24-blocked-25-hydroxyvitamin D derivatives generally being given in doses of 1–10 mg per animal, while in the case of the corresponding 24-blocked $1\alpha$-hydroxylated compounds, dosages of 0.1–1 mg per animal are effective.

The administration of a combination of the active 24-blocked vitamin D compounds is also possible and effective. Such combinations most advantageously involve the co-administration of a 25-hydroxyvitamin D compound and a 1-hydroxyvitamin D analog. For example, the administration of a 24-blocked-25-hydroxyvitamin D compound together with the corresponding 24-blocked-$1\alpha$-hydroxyvitamin D compound in a ratio preferably adjusted so as to provide the 25-hydroxy compound in about 5–10 fold excess over the $1\alpha$-hydroxylated material in a highly effective method of treatment.

Any conventional route of administration may be used. For example, the compounds, dissolved in an innocuous oil conventionally used in veterinary practice, such as corn oil, sesame oil, propylene glycol, etc., can be administered by an intramuscular or subcutaneous injection, or may be applied as a solution in a solvent such as dimethylsulfoxide for transcutaneous absorption. Alternatively, the compounds can be administered after compounding with other materials, as a bolus, or in encapsulated form or, again with suitable adjuvants, or in a suitable solvent, as a top dressing for grains or other dietary components fed to the animals.

Illustrative examples of specific compounds which are effective is preventing milk fever disease and of protocols for their administration are set forth below.

1. 24-blocked-25-hydroxyvitamin D 24,24-fluoro-25-hydroxyvitamin $D_3$ dissolved in corn oil is given by intramuscular injection to high-producing cows which are characterized by having a propensity toward milk fever disease in an amount sufficient to supply each animal with about 4 mg of the compound. The injection is made five days prior to the expected calving date and is effective in preventing milk fever disease.

2. 24-blocked 1α-hydroxyvitamin D 24,24-difluoro-1α,25-dihydroxyvitamin $D_3$ dissolved in corn oil, when given to cows having a tendency toward milk fever, by intramuscular injection in an amount to provide each animal with about 0.4 mg five days prior to calving is effective to prevent milk fever.

3. 24-blocked-25-hydroxyvitamin D in combination with 24-blocked-1α-hydroxyvitamin D 24,24-difluoro-25-hydroxyvitamin $D_3$ and 24,24-difluoro-1α,25-dihydroxyvitamin $D_3$ dissolved in corn oil in the ratio of 10:1 are given by intramuscular injection to cows characterized by a high incidence of milk fever disease five days prior to calving. Sufficient of the solution is given to provide each animal with about 4 mg and 0.4 mg respectively of the 24-blocked-25-hydroxyvitamin $D_3$ and the 24-blocked-1α,25-dihydroxyvitamin $D_3$ compounds. The admixture of the compounds is effective is preventing milk fever.

In all cases with the administration of the 24-blocked vitamin D compounds in accordance with the present invention, if calving does not occur within the expected time after first administration of the compound, generally five days, a repeat injection of the compound may be given. In fact, a third dose of the compound may be given if after an additional five days the cows has not calved.

It is to be appreciated that the dosages specified above are not necessarily critical. Dosages can, of course, vary with the size of the cow to which it is being administered. In any event sufficient of the material must be given in all cases to accomplish the desired end of preventing milk fever disease. Administration of amounts in excess of such amounts should be avoided as economically unsound.

We claim:

1. The method for treatment and prophylaxsis for milk fever disease in dairy cattle which comprises administering to said cattle prior to parturition a vitamin D derivative, which is characterized by the presence of a hydroxyl group at at least one of the C-1 and C-25 positions and a halogen substituent at the C-24 position in the molecule, in an amount sufficient to induce said treatment and prophylaxsis.

2. The method of claim 1 wherein the blocking group at the C-24 position is selected from 24-monofluoro or 24-difluoro.

3. The method of claims 1 or 2 wherein the vitamin D derivative is 25-hydroxylated.

4. The method of claim 1 or 2 wherein the vitamin D derivative is 1α-hydroxylated.

5. The method of claims 1 or 2 wherein the vitamin D derivative is 1α,25-dihydroxylated.

6. The method of claim 3 wherein the vitamin D derivative is selected from 24,24-difluoro-25-hydroxyvitamin $D_3$ and 24-fluoro-25-hydroxyvitamin $D_3$ and 24-fluoro-1-hydroxyvitamin $D_2$.

7. The method of claim 6 wherein the vitamin D derivative is 24,24-difluoro-25-hydroxyvitamin $D_3$.

8. The method of claim 5 wherein the vitamin D derivative is selected from 24,24-difluoro-1α,25-dihydroxyvitamin $D_3$ and 24-fluoro-1α,25-dihydroxyvitamin $D_3$.

9. The method of claim 8 wherein the vitamin D derivative is 24,24-difluoro-1α,25-dihydroxyvitamin $D_3$.

10. The method of claim 1 wherein the vitamin D derivative is administered in an admixture of 24,24-difluoro-25-hydroxyvitamin $D_3$ and 24,24-difluoro-1α,25-dihydroxyvitamin $D_3$.

11. The method of claim 10 in which the 24,24-difluoro-25-hydroxyvitamin $D_3$ and 24,24-difluoro-1α,25-dihydroxyvitamin $D_3$ are present respectively in the admixture in a ratio of from about 5:1 to about 10:1.

12. The method of claim 1 the vitamin D derivatives are administered in an amount from about 0.1 to about 10 mg per animal from about 4 to 8 days prior to calving.

13. The method of claim 12 wherein the vitamin D derivatives are administered by injection.

14. The method of claim 13 wherein the injection is intramuscular.

15. The method of claim 13 wherein the injection is subcutaneous.

16. The method of claim 12 wherein the vitamin D derivatives are administered orally.

* * * * *